(12) United States Patent
Fisker

(10) Patent No.: US 11,202,690 B2
(45) Date of Patent: Dec. 21, 2021

(54) METHOD OF DIGITALLY DESIGNING A MODIFIED DENTAL SETUP

(71) Applicant: 3Shape A/S, Copenhagen K (DK)

(72) Inventor: Rune Fisker, Virum (DK)

(73) Assignee: 3SHAPE A/S, Copenhagen K (DK)

( * ) Notice: Subject to any disclaimer, the term of this patent is extended or adjusted under 35 U.S.C. 154(b) by 530 days.

(21) Appl. No.: 15/529,771

(22) PCT Filed: Nov. 26, 2015

(86) PCT No.: PCT/EP2015/077801
§ 371 (c)(1),
(2) Date: May 25, 2017

(87) PCT Pub. No.: WO2016/083519
PCT Pub. Date: Jun. 2, 2016

(65) Prior Publication Data
US 2017/0319293 A1    Nov. 9, 2017

(30) Foreign Application Priority Data
Nov. 27, 2014  (DK) ............................ PA 2014 70741

(51) Int. Cl.
*A61C 7/00*       (2006.01)
*A61C 5/77*       (2017.01)
(Continued)

(52) U.S. Cl.
CPC ................. *A61C 7/002* (2013.01); *A61C 5/77* (2017.02); *A61C 9/004* (2013.01); *A61C 9/0053* (2013.01); *G16H 20/40* (2018.01)

(58) Field of Classification Search
CPC ......... A61C 7/002; A61C 5/77; A61C 9/0053; A61C 13/0004; A61C 9/004; G16H 20/40
See application file for complete search history.

(56) References Cited

U.S. PATENT DOCUMENTS

| 7,234,937 B2 * | 6/2007 | Sachdeva | A61C 7/00 433/24 |
| 2002/0010568 A1 * | 1/2002 | Rubbert | A61C 7/00 703/6 |

(Continued)

FOREIGN PATENT DOCUMENTS

| WO | WO 2006/065955 A2 | 6/2006 |
| WO | WO 2009/010543 A1 | 1/2009 |

(Continued)

OTHER PUBLICATIONS

International Search Report (PCT/ISA/210) dated Feb. 22, 2016, by the European Patent Office as the International Searching Authority for International Application No. PCT/EP2015/077801.

(Continued)

*Primary Examiner* — Heidi M Eide
(74) *Attorney, Agent, or Firm* — Buchanan Ingersoll & Rooney P.C.

(57) ABSTRACT

A method for digitally designing a modified dental setup up on a digital 3D dental model representing at least a part of the jaws of a patient includes the steps of obtaining a pre-treatment digital 2D image of at least a part of the patient's teeth, obtaining a digital 3D representation of the at least a part of the patient's set of teeth, obtaining a proposed digital 2D image of a desired dental setup based on the pre-treatment digital 2D image, wherein at least one digital tooth modification has been provided, and transferring the at least one digital tooth modification from the proposed digital 2D image to the digital 3D representation. This provides a method where the practitioner with relative simple means can present the patient with a visualization of an expected outcome of a dental treatment.

9 Claims, 2 Drawing Sheets

(51) Int. Cl.
*A61C 9/00* (2006.01)
*G16H 20/40* (2018.01)

(56) References Cited

U.S. PATENT DOCUMENTS

| | | | |
|---|---|---|---|
| 2003/0143509 A1* | 7/2003 | Kopelman | A61C 7/00 433/24 |
| 2007/0141534 A1 | 6/2007 | Wen | |
| 2009/0316996 A1 | 12/2009 | Marshall et al. | |
| 2010/0145898 A1 | 6/2010 | Malfliet et al. | |
| 2013/0158958 A1* | 6/2013 | Methot | A61C 13/0004 703/1 |
| 2013/0218530 A1* | 8/2013 | Deichmann | A61C 13/0004 703/1 |
| 2014/0011162 A1 | 1/2014 | Zegarelli | |
| 2014/0342304 A1 | 11/2014 | Meletiou, Jr. | |

FOREIGN PATENT DOCUMENTS

| | | |
|---|---|---|
| WO | WO 2009/141248 A1 | 11/2009 |
| WO | WO 2012/006717 A1 | 1/2012 |
| WO | WO 2013/034462 A2 | 3/2013 |
| WO | WO 2013/034462 A3 | 3/2014 |
| WO | WO 2014/135695 A1 | 9/2014 |

OTHER PUBLICATIONS

Written Opinion (PCT/ISA/237) dated Feb. 22, 2016, by the European Patent Office as the International Searching Authority for International Application No. PCT/EP2015/077801.

"Marker-Free Human Motion Capture: Estimation Concepts and Possibilities with Computer Vision Techniques from a Single Camera View Point" by Daniel Grest, published by Lap Lambert 15 Academic Publishing (Jul. 22, 2010), ISBM-13:978-3838382227.

Communication issued in corresponding European Patent Application No. 15800874.8-1126, dated Oct. 24, 2018 (4 pages).

Office Action issued in corresponding European Patent Application No. 15800874.8, dated Nov. 13, 2019 (4 pages).

* cited by examiner

METHOD OF DIGITALLY DESIGNING A MODIFIED DENTAL SETUP

FIELD OF THE INVENTION

This invention generally relates to a method for designing a digital 3D dental model having a modified dental setup. The modified dental setup represents a proposed dental setup for a patient and is used for designing a dental restoration or planning an orthodontic treatment. In particular the digital 3D dental model is obtained by using simple design tools that allows the patient to get a good presentation of the expected esthetic result of a proposed dental treatment.

BACKGROUND OF THE INVENTION

Today dental treatment is not only about treating cavities, repair broken teeth or correct malocclusion. It is also important to be able to give a patient an esthetically pleasing smile while maintaining the function.

This have caused a multitude of planning tools wherein the patient is presented with expected treatment results in order to enable the patient to visualize the resulting smile.

However, these planning tools often have no link between the presentation part and the actual design part and although many dental technicians are very capable there is still a need to improve consistency between the proposed smile and the actual resulting smile.

Moreover, there exists a need to be able to do this with relative simple means.

SUMMARY

In one aspect herein there is disclosed a method for digitally designing a modified dental setup on a digital 3D dental model representing at least a part of the teeth of a patient comprising the steps of:
obtaining a pre-treatment digital 2D image of at least a part of the teeth of the patient,
obtaining a digital 3D representation of the at least a part of the teeth of the patient,
obtaining a proposed digital 2D image of a desired dental setup based on the pre-treatment digital 2D image, wherein at least one digital tooth modification has been provided,
transferring the at least one digital tooth modification from the proposed digital 2D image to the digital 3D representation.

This provides a method where the practitioner with relative simple means can present the patient with a visualization of an expected outcome of a dental treatment. In particular the final treatment result can be expected to correspond to the proposed digital 2D image since the result is designed based on the suggestions made to the patient during the planning phase.

Accordingly, the method has the advantage that the patient, can trust that the esthetic smile presented before treatment correspond to, or is very similar to, the resulting smile.

The method disclosed herein is suitable for planning different types of treatments.

Accordingly, in one aspect the method disclosed herein is used for restorative treatment. Thus, in one embodiment the method comprises designing a digital dental restoration based on the at least one tooth modification.

In another aspect the method disclosed herein is suited for orthodontic treatment. Accordingly, in one embodiment the method comprises planning an orthodontic treatment based on the at least one tooth modification.

In order to enable the user to design a modified dental setup based on the digital tooth modification, the digital tooth modification needs to be transferred to the digital representation.

Said in terms typically used when working with digital design environments such as CAD software, the at least one digital tooth modification and the digital 3D representation should be presented/placed in the same coordinate system.

In one embodiment this can be done by establishing a transformation that tells the computer how the at least one digital tooth modification should be placed in the coordinate system of the digital 3D representation. Of course, such transformation is relative and it can also be used to place the digital 3D representation in the coordinate system of the at least one digital tooth modification.

In other words, a transformation comprises information telling the computer how two independent digital 3D models should be placed relative to each other.

Such a transformation is typically expressed by a transformation matrix. The transformation matrix comprises information on position, translation and rotation in order to sufficiently describe a transformation of a rigid object.

Accordingly, in one embodiment the step of transferring the at least one digital tooth modification from the proposed digital 2D image to the digital 3D representation further comprises:
determining a transformation by estimating the camera view for the pre-treatment digital 2D image based on a correlation of at least one facial feature in the pre-treatment digital 2D image and corresponding at least one facial feature in the digital 3D representation, and
transferring the at least one digital tooth modification from the proposed digital 2D image to the digital 3D representation according to the transformation.

In the current embodiment it is advantageous that the transformation can be established based on the pre-treatment digital 2D image and the digital 3D representation. The reference used to establish the transformation is the facial feature, for example at least a part of one or more of the teeth visible in the digital pre-treatment 2D image and represented in the digital 3D representation. As mentioned, this allows the practitioner to use relative cheap equipment such as a digital camera to take a picture of the patient and use that picture to establish a proposed treatment result.

For example, the transformation may be determined by estimating the camera view, e.g. the perspective, zoom, position and/or rotation of the physical camera that was used to obtain the digital pre-treatment 2D image. This can for example be done by having the user identifying corresponding points on the digital pre-treatment 2D image and the digital 3D representation. Such corresponding points will typically use a facial feature such as at least a part of one or more of the teeth visible in the digital pre-treatment 2D image, which can be easily identified in the digital 3D representation.

For example with four corresponding points identified in both the digital pre-treatment 2D image and the digital 3D representation, the software is able to estimate the camera position and field of view used when, the digital pre-treatment 2D image was taken. These parameters may then be used to transfer the digital tooth modification to the view of the digital 3D representation as we know that the digital pre-treatment 2D image and the proposed digital 2D image are shown from the same perspective and camera position. The principles hereof are for example described in "Marker- Free Human Motion Capture: Estimation Concepts and Possibilities with Computer Vision Techniques from a Single Camera View Point" by Daniel Grest, published by LAP LAMBERT 15 Academic Publishing (Jul. 22, 2010), ISBM-13:978-3838382227. This principle is also described and used in published international application WO 2014/135695.

The transformation could also be determined completely manually by having the user align the digitally pre-treatment 2D image and the digital 3D representation.

The 2D images, i.e. the pre-treatment and proposed digital 2D images, may be visually presented together or separately with the digital 3D representation if so desired. This can for example be done by overlaying the respective 2D images based on the determined transformation.

When the at least one digital tooth modification has been transferred to the digital 3D representation it can be used as basis for designing a modified dental setup in any number of ways.

For example, the digital tooth modification may simply be superimposed or overlaid on the digital 3D representation as a design guide. This gives the user a visual indication of where a restoration should be designed or where a tooth should be moved.

In another example, the transferred digital tooth modification can be used as a confinement shell. E.g. it will prevent the user to design outside its boundaries or warn the user when the boundaries are crossed.

In yet another example the transferred digital tooth modification is generated as a digital model of a tooth anatomy. This digital model can be used as basis for designing a dental restoration such as a veneer or a crown.

In one embodiment the method comprises
selecting the tooth modification from a teeth library comprising at least one library 2D digital tooth modification, wherein the teeth library comprises a corresponding library 3D digital tooth modification for the at least one library 2D digital tooth modification, This advantageously creates a link between a 2D representation of the digital tooth modification and a 3D representation of the digital tooth modification, which is particular advantageous when designing restoration, in particular crowns.

For example, teeth library may be in the form of a digital database comprising library digital 2D representations of standard teeth. Each library digital 2D representation of a tooth is linked to a unique library 3D representation of the same tooth. Thus, when the user selects a library 2D digital tooth representation from the database its library 3D digital tooth modification counterpart is identified. Accordingly, as the digital tooth modification is transferred from the proposed 2D image to the digital 3D representation the library 2D digital tooth modification can be replaced with the corresponding library 3D digital tooth modification.

In order to provide the at least one digital tooth modification a number of different solutions can be provided.

In one embodiment the method comprises
segmenting at least a part of a tooth in the pre-treatment digital 2D image,
generating the at least one digital tooth modification based on the segmented part of the tooth.

By segmentation the pre-treatment digital 2D image is altered in order to provide the proposed digital 2D image. The segmented part may be modified or replaced by a new representation of the segmented tooth. Moreover, any changes to the segmented part that alters it size will also modify the shape of the digital 2D image that borders the segmented part.

In another embodiment the method further comprises
generating the at least one digital tooth modification as an overlay on the pre-treatment digital 2D image, This does not alter the pre-treatment digital 2D image but creates a proposed digital 2D image wherein the digital tooth modification is overlaid onto the pre-treatment digital 2D image.

In some situations, it may be relevant to evaluate a suggested treatment result from different angles.

Accordingly, in one embodiment the method further comprises,
obtaining at least two pre-treatment digital 2D images from different angles, and
obtaining at least two proposed digital 2D images, each corresponding to one respective pre-treatment digital 2D image, wherein the at least one digital tooth modification has been provided in each of the proposed digital 2D images.

During treatment planning or treatment itself the dentist may find it necessary to rescan the patient's teeth. This can for example be the case where orthodontic treatment has been deemed necessary before restorative work is done.

Accordingly, in one embodiment the method comprises
obtaining an intermediate 3D representation of the patient's set of teeth after partial treatment, wherein at least one tooth has been modified,
transferring the at least one digital tooth modification to the intermediate 3D representation.

The method for digitally designing the modified dental setup is preferably executed on a computer. E.g. a data storage medium, such as a hard drive, stores computer code, which when executed by a data processor performs one or more of the steps of the method.

For example the step of obtaining the pre-treatment digital 2D image may involve loading a data file from an external data source. However, it may also involve the actual step of taking the picture.

Similarly, the step of obtaining the digital 3D representation may involve loading it from an external data source, but may also involve the actual step of scanning. This can for example be the scanning of a model or scanning the jaw of the patient as known in the art.

The step of obtaining the proposed digital 2D image typically requires the user to interact with a digital design environment in order to create the at least one digital tooth modification. Accordingly, the computing device comprises an input interface for receiving user input. This can for example be a mouse or a touch screen. In order to visualize the design process and present it to the user and the patient an output interface can be provide. This will typically be a display unit.

The step of transferring the at least one digital tooth modification is preferably done by the processing unit according to a set of requirements as described herein. However, the user may provide certain input to initiate the transfer process or modify the transfer manually if so desired.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein.

DETAILED DESCRIPTION

In the following description, reference is made to the accompanying figures, which show by way of illustration how the invention may be practiced.

Figure 1:
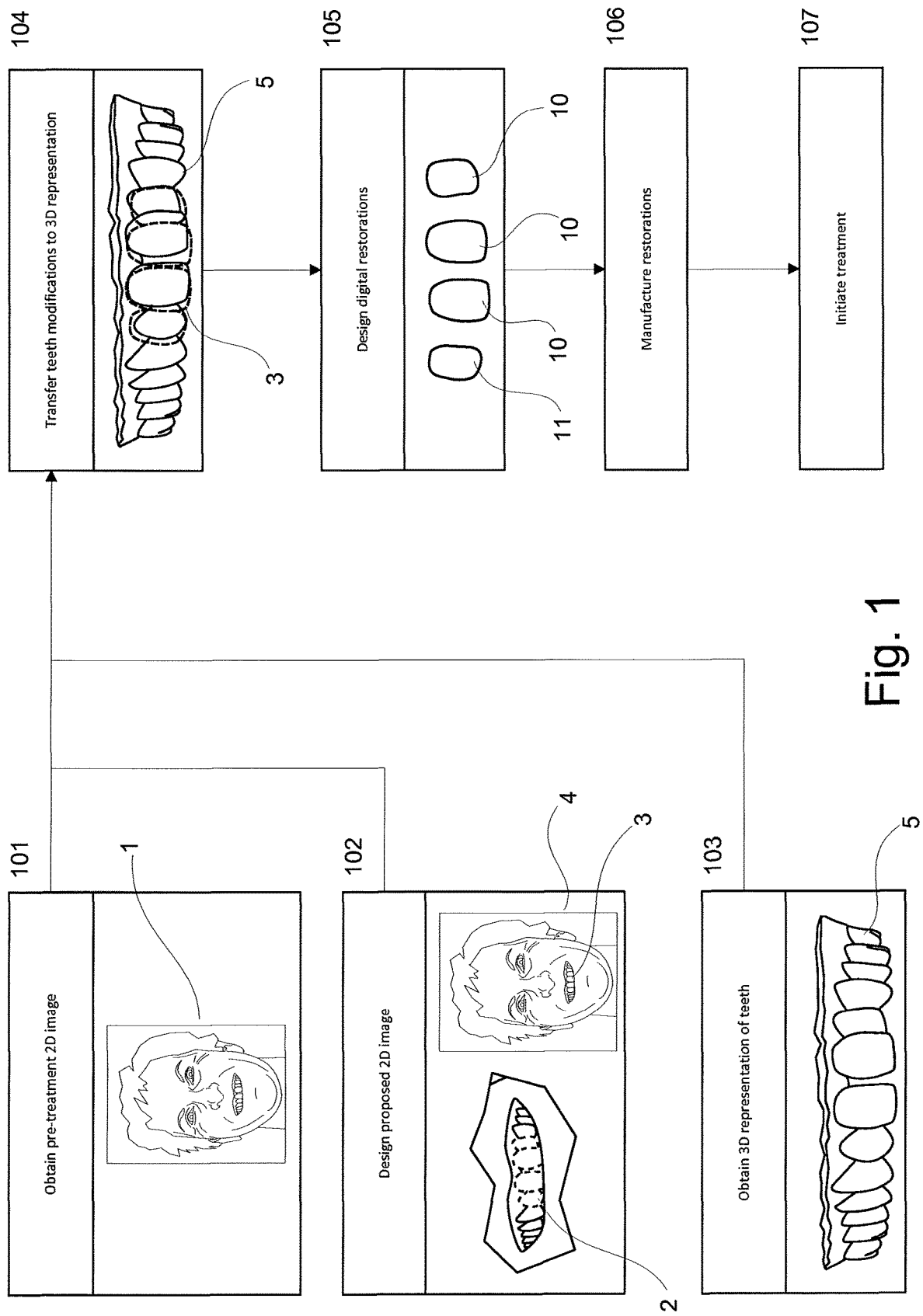
FIG. 1 shows a diagram of one embodiment of a workflow using the method as described herein.

In one embodiment of the invention as disclosed herein, it is incorporated in a work flow as shown in FIG. 1.

The workflow involves a number of steps 101, 102, 103 and 107 during which the patient is at the dentist, so-called patient time. Steps 104, 105 and 106 may be performed without the need of the patient.

In step 101 a 2D image 1 is obtained of the patient. The 2D image is a digital image taken by a standard camera, for example the camera on the dentist's smart phone. The 2D image shows the smile of the patient wherein a part of the upper anterior teeth are visible.

The image is then loaded on to a computing device, such as a laptop, desktop or a tablet.

On the computing device the dentist identifies the teeth or areas where restorative work is to be performed. The software on the computing device then segments that area 2. An input interface allows the dentist to make manual changes to the segmentation if necessary.

After the segmentation has been performed the dentist may manipulate the shape and/or shade of the existing teeth in the 2D image or he can import 2D digital tooth representations from a database in order to provide teeth modifications 3.

Manipulating the shape and/or shade of the existing teeth is typically done when minor restorative work is done, such as veneers or inlays. Import of 2D digital tooth representations is typically done when teeth are planned to be ground down and new crowns are to be placed on the prepped teeth. However, the dentist may chose whatever process is best suited for the current case or use them together with each other, e.g. import a 2D digital tooth representation and then further manipulate the shape, thereof.

After manipulation a proposed digital 2D image 4, which shows the teeth modifications is presented to the patient. The proposed digital 2D image can be shown together with the pre-treatment 2D image of the patient in order to give the patient an idea of how the changes will affect his/hers appearance. The dentist can easily do changes to the proposed digital 2D image together with the patient if desired.

After the patient accepts the proposed digital 2D image the dentist will obtain a digital 3D representation 5 of the patient's teeth in the area where restorative work is to be done. The dentist may obtain a digital 3D representation of all the teeth, i.e. the full dental setup of patient, or just the relevant teeth wherein dental treatment is to be performed. This can be done in different ways, but in the current example the dentist scans the patient using an intra-oral scanner such as the TRIOS scanner manufactured by 3Shape A/S.

Based on the proposed digital 2D image and the digital 3D representation a restoration can be designed that provides a result very close to the one in the proposed digital 2D image.

This is done by transferring the digital tooth modification to the digital 3D representation in step 104.

The transfer is done by estimating a transformation for the digital 3D representation in order to align it with the view of the pre-treatment digital 2D image and then applying that transformation to the teeth modifications in the proposed digital 2D image.

As described previously this can be done by identifying corresponding points on the pre-treatment 2D image and the digital 3D representation.

With the teeth modifications 3 transferred to the digital 3D representation the dentist and the dental lab can discuss and agree on a treatment plan in order to give the patient the desired esthetics as shown in the proposed digital 2D image.

For example, in the current case treatment should be initiated by moving the left central incisor using orthodontics. After this veneers 10 are designed for the central incisors and the left incisor and a full crown 11 is designed for the right incisor in step 105.

Of course, if significant changes are done to the dental setup, e.g. by using orthodontic treatment, the patient should be rescanned in order to obtain a 3D representation of the intermediate dental setup. The rescan is however easily aligned with the teeth modifications by replacing the initial digital 3D representation after aligning the two 3D representations. The alignment can for example be done by using unmodified parts of the digital 3D representation of the intermediate dental setup as reference when aligning with the initial digital 3D representation.

With the restorations designed in the digital workspace and, the modified; dental setup design is complete, the restorations can be sent to manufacturing in step 106. The manufacturing can be any suitable digital manufacturing process such as milling or printing. Such types of manufacturing and variations thereof are well known in the art and depending on the type of restoration and on the material one manufacturing process may be more advantageous than the other.

Finally, in step 107 the dentist receives the manufactured dental restorations and can initiate treatment.

As mentioned, the method as disclosed herein is very suitable for practitioners and their assistants for visualizing the expected treatment outcome for a patient or as confirmation for themselves in a simple and reliable manner.

Figure 2:
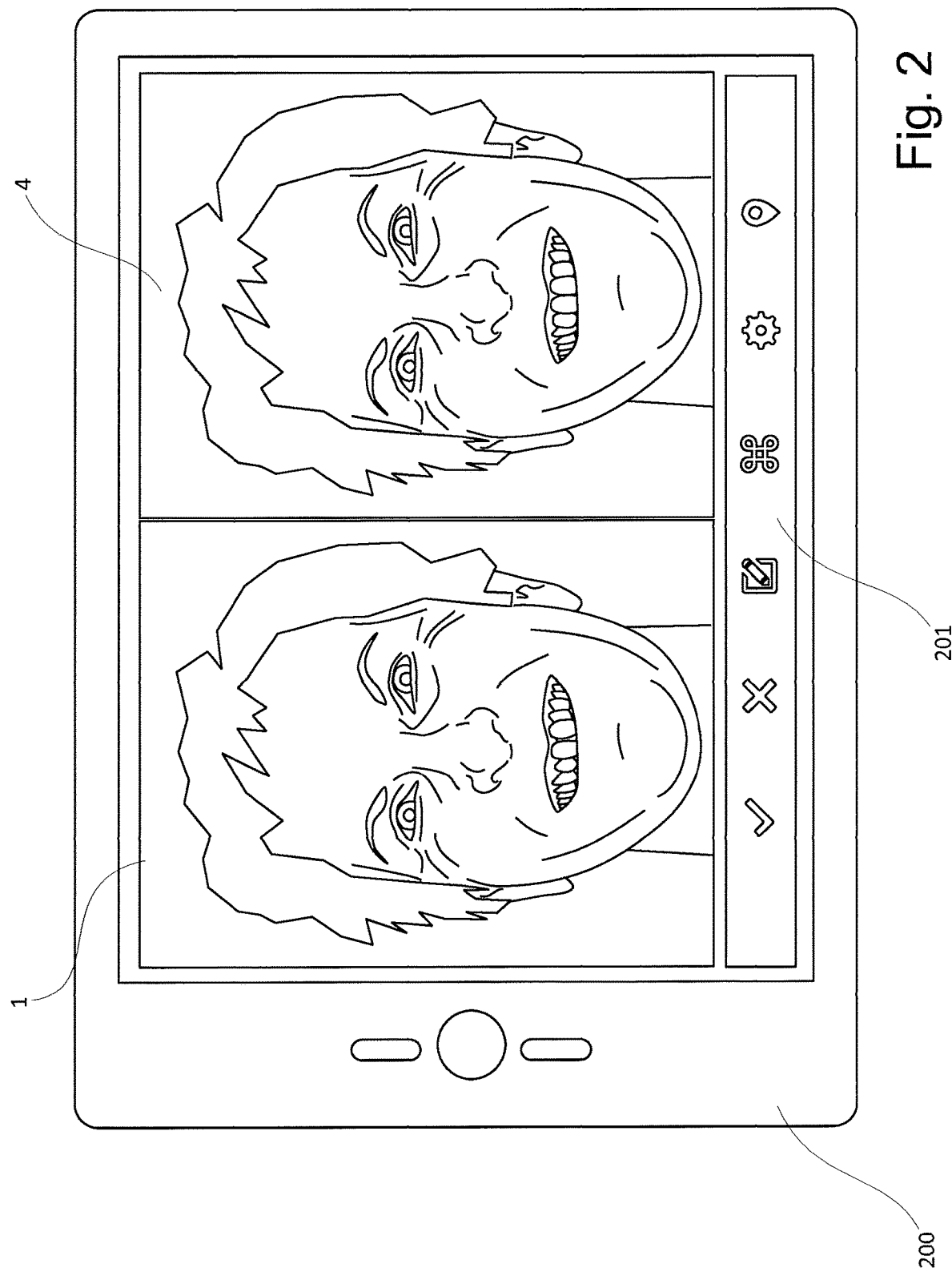
FIG. 2 shows a computing device using an interface suited for involving the patient in the design process.

For example as shown in FIG. 2, a tablet 200 is used to provide the proposed digital 2D image 4. The dentist and the patient can together sit and design teeth modifications using the design tools 201 and see the actual changes and the pre-treatment digital 2D image 1 compared with the proposed digital 2D image 4.

The method as disclosed herein subsequently provides support for the user designing the dental restoration based on the teeth modifications and this enables the resulting esthetics of the patient's smile be very similar to that presented to the patient before treatment.

Although some embodiments have been, described and shown in detail, the invention is not restricted to them, but may also be embodied in other ways within the scope of the subject matter defined in the following claims. In particular, it is to be understood that other embodiments may be utilised and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

A claim may refer to any of the preceding claims, and "any" understood to mean "any one or more" of the preceding dams.

It should be emphasized that the term "comprises/comprising" when used in, this specification is taken to specify the presence of stated features, integers, steps or components but does not preclude the presence or addition of one or more other features, integers, steps, components or groups thereof.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hardwired circuitry instead of software or in combination with software.

The invention claimed is:

1. A method for digitally designing a modified dental setup on a digital 3D dental model representing at least a part of the teeth of a patient comprising the steps of:
    using a camera to obtain a pre-treatment digital 2D image of at least a part of the teeth of the patient,
    obtaining a digital 3D representation of the at least a part of the teeth of the patient,
    modifying the pre-treatment digital 2D image to obtain a proposed digital 2D image of a desired dental setup based on the pre-treatment digital 2D image, wherein at least one digital tooth modification is obtained,
    determining a transformation for the digital 3D representation in order to align it with a view of the pre-treatment digital 2D image by estimating a camera view of the camera used to obtain the pre-treatment digital 2D image by identifying corresponding points of at least one facial feature in the pre-treatment digital 2D image and corresponding at least one facial feature in the digital 3D representation, and
    transferring the at least one digital tooth modification from the proposed digital 2D image to the digital 3D representation according to the transformation.

2. A method according to claim 1, wherein the method further comprises:
    designing a digital dental restoration based on the at least one tooth modification.

3. A method according to claim 1, wherein the method further comprises:
    planning an orthodontic treatment based on the at least one tooth modification.

4. A method according to claim 1, wherein modifying the pre-treatment digital 2D image comprises:
    selecting the tooth modification from a teeth library comprising at least one library 2D digital tooth modification, wherein the teeth library comprises a corresponding library 3D digital tooth modification for the at least one library 2D digital tooth modification.

5. A method according to claim 1, wherein the method further comprises:
    segmenting at least a part of a tooth in the pre-treatment digital 2D image,
    generating the at least one digital tooth modification based on the segmented part of the tooth.

6. A method according to claim 1, wherein the method further comprises:
    generating the at least one digital tooth modification as an overlay on the pre-treatment digital 2D image.

7. A method according to claim 1, wherein the method further comprises:
    obtaining an additional pre-treatment digital 2D image from an angle different from an angle at which the pre-treatment digital 2D image was taken, and
    obtaining an additional proposed digital 2D image, each of the proposed digital 2D images corresponding to one respective pre-treatment digital 2D image, wherein the at least one digital tooth modification has been provided in each of the proposed digital 2D images.

8. A method according to claim 1, wherein the at least one digital tooth modification is transferred to the digital 3D representation by using at least a part of one or more of the teeth visible in the pre-treatment digital 2D image and in the digital 3D representation as a reference.

9. A method for digitally designing a modified dental setup on a digital 3D dental model representing at least a part of the teeth of a patient, the method comprising the steps of:
    using a camera to obtain a pre-treatment digital 2D image of at least a part of the teeth of the patient,
    obtaining a digital 3D representation of the at least a part of the teeth of the patient,
    modifying the pre-treatment digital 2D image to obtain a proposed digital 2D image of a desired dental setup based on the pre-treatment digital 2D image, wherein at least one digital tooth modification is obtained,
    transferring the at least one digital tooth modification from the proposed digital 2D image to the digital 3D representation,
    obtaining an intermediate digital 3D representation of the patient's set of teeth after a partial treatment, wherein at least one tooth has been modified, wherein the intermediate digital 3D representation reflects the partial treatment, and
    transferring the at least one digital tooth modification to the intermediate 3D representation by aligning the at least one digital tooth modification with the intermediate digital 3D representation.

* * * * *